United States Patent
Davis et al.

(10) Patent No.: US 10,563,647 B2
(45) Date of Patent: Feb. 18, 2020

(54) LOW-FORCE PUMPING SEGMENT

(71) Applicant: CareFusion 303, Inc., San Diego, CA (US)

(72) Inventors: Lisa Davis, San Diego, CA (US); Robert Dwaine Butterfield, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 179 days.

(21) Appl. No.: 15/597,094

(22) Filed: May 16, 2017

(65) Prior Publication Data

US 2017/0248134 A1    Aug. 31, 2017

Related U.S. Application Data

(63) Continuation of application No. 13/228,311, filed on Sep. 8, 2011, now Pat. No. 9,683,562.

(51) Int. Cl.
| | | |
|---|---|---|
| *F04B 43/00* | (2006.01) |
| *A61M 39/08* | (2006.01) |
| *F04B 43/12* | (2006.01) |
| *F04B 43/08* | (2006.01) |
| *A61M 5/142* | (2006.01) |

(52) U.S. Cl.
CPC ......... *F04B 43/0072* (2013.01); *A61M 39/08* (2013.01); *F04B 43/082* (2013.01); *F04B 43/12* (2013.01); *A61M 5/14228* (2013.01)

(58) Field of Classification Search
CPC ............... A61M 39/08; A61M 5/14228; F04B 43/0072; F04B 43/082; F04B 43/12
See application file for complete search history.

(56) References Cited

U.S. PATENT DOCUMENTS

| | | | |
|---|---|---|---|
| 4,409,489 A | 10/1983 | Hayes | |
| 4,936,760 A * | 6/1990 | Williams | ............... A61M 5/142 417/478 |
| 5,088,522 A | 2/1992 | Rath et al. | |
| 5,281,112 A | 1/1994 | Montoya et al. | |
| 5,336,051 A | 8/1994 | Tamari | |
| 5,486,099 A | 1/1996 | Montoya | |
| 5,964,583 A | 10/1999 | Danby | |
| 6,171,082 B1 | 1/2001 | Hankner et al. | |
| 2005/0209563 A1 | 9/2005 | Hopping et al. | |
| 2009/0259089 A1 | 10/2009 | Gelbart et al. | |
| 2011/0152831 A1* | 6/2011 | Rotem | ............... A61M 5/14228 604/506 |

OTHER PUBLICATIONS

International Search Report and Written Opinion for PCT/US2012/051637, dated Feb. 2013.

\* cited by examiner

*Primary Examiner* — Brandy S Lee
(74) *Attorney, Agent, or Firm* — Morgan, Lewis & Bockius LLP (57) ABSTRACT

A pumping segment having a low shut-off force is disclosed. The pumping segment includes a tube having an interior surface with at least two notches on opposite sides of the interior surface.

15 Claims, 5 Drawing Sheets

FIG. 7

LOW-FORCE PUMPING SEGMENT

CROSS-REFERENCES TO RELATED APPLICATIONS

This application is a continuation application of U.S. patent application Ser. No. 13/228,311, filed Sep. 8, 2011, which is hereby incorporated by reference in its entirety for all purposes.

BACKGROUND

Field

The present disclosure is related to infusion pumps and, in particular, to the tubing used in the intravenous (IV) sets that are used with infusion pumps.

Description of the Related Art

Patients in hospitals are often provided with medical fluids that are administered through an IV infusion. Many infusion pumps operate using a peristaltic mechanism having a series of compressor blocks, or fingers, that sequentially compress and release segments of a flexible tube that is part of the IV set, commonly referred to as the "pumping segment" of the IV set, connecting the source of medical fluid, such as an IV bag, to the patient. This type of mechanism relies on the resilience of the tube to expand the tube when the compressive force is removed, thereby increasing the cross-sectional area of the tube under that finger.

Selection of a tube material having the flexibility to withstand repeated compressions while also having the necessary resilience to rebound between compressions as well as low gas permeability, to minimize the amount of air introduced into the fluid within the tube, is a challenge. A typical round tube must be compressed beyond the point at which the interior wall touches in order to completely close off the tube. This "overcompression" of the tube requires a significant application of force by the pump as well as creating additional stress in the tube walls as they are stretched during the overcompression. One commonly selected tube material is silicone, although silicone is relatively expensive and has a relatively high gas permeability.

SUMMARY

It is desirable to provide a pumping mechanism that can be used in a peristaltic-type of pump that requires less force, compared to existing systems, to completely close off the pumping segment. It would be advantageous if this low-force pumping segment were backwards compatible with existing peristaltic pumping mechanisms.

In certain embodiments, a pumping segment with a low shut-off force is provided. The pumping segment includes a tube having an interior surface with at least two sharp notches on opposite sides of the interior surface.

In certain embodiments, an IV set with a low shut-off force is provided. The IV set includes a tube having an interior surface with at least two sharp notches on opposite sides of the interior surface. Each notch has a tip. The notches divide the tube into upper and lower portions.

In certain embodiments, an IV pump configured to provide a low shut-off force is disclosed. The IV pump is configured to accept a pumping segment having an interior surface and at least two sharp notches on opposite sides of the interior surface. Each notch has a tip and the notches divide the tube into upper and lower portions having respective constant wall thicknesses between the tips. The IV pump is further configured to compress the upper and lower portions to a combined thickness that is approximately equal to a sum of the thicknesses of the upper and lower portions of the pumping segment.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The following description discloses embodiments of a low-force pumping segment suitable for incorporation into an IV set intended for use with a peristaltic IV pump. In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. The systems and methods disclosed herein are discussed in the context of a medical fluid being administered to a patient via infusion in a healthcare facility. Nothing herein should be interpreted to limit the coverage of the claims to a healthcare environment or to medical treatment unless specifically stated as such.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

Figure 1A:
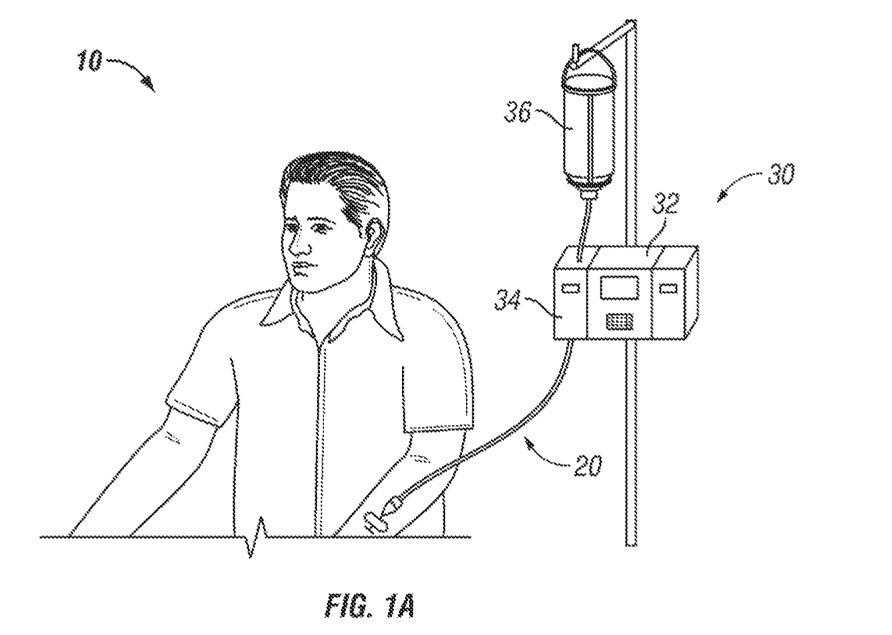
FIG. 1A illustrates a patient receiving an infusion of a medical fluid through an IV pump according to certain aspects of the present disclosure.

FIG. 1A illustrates a patient 10 receiving an infusion of a medical fluid through an IV pump 30 according to certain aspects of the present disclosure. The IV pump 30 comprises a controller 32 and two pump modules 34. An IV set 20 is connected between a container 36 of the medical fluid and the patient 10. The IV set 20 is described in greater detail with respect to FIG. 1B.

Figure 1B:
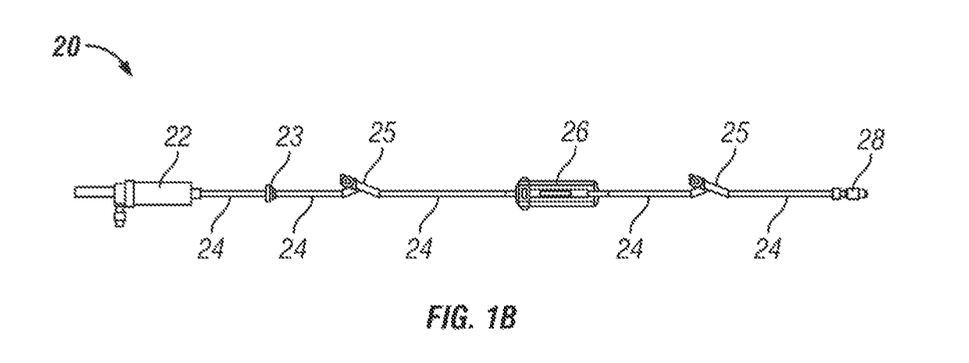
FIG. 1B depicts an exemplary IV set according to certain aspects of the present disclosure.
Figure 2A:
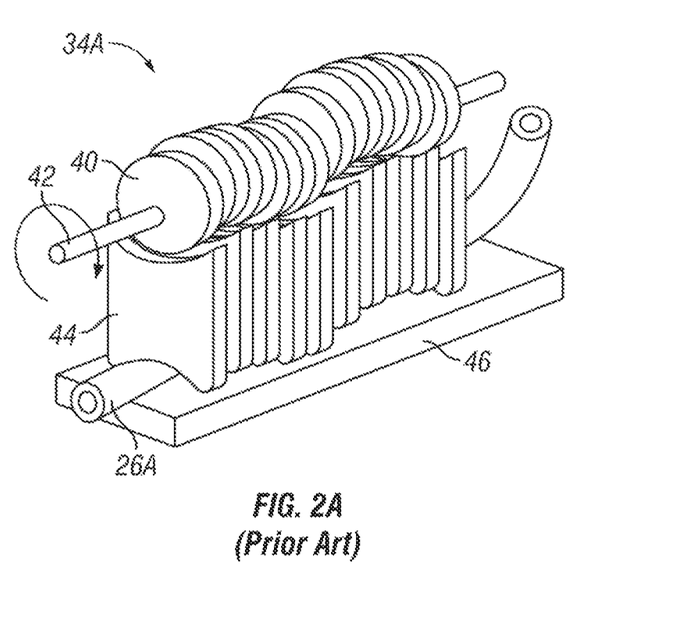
FIGS. 2A and 2B are a perspective view and a cross-section view, respectively, of a peristaltic pumping mechanism according to certain aspects of the present disclosure.
Figure 2B:
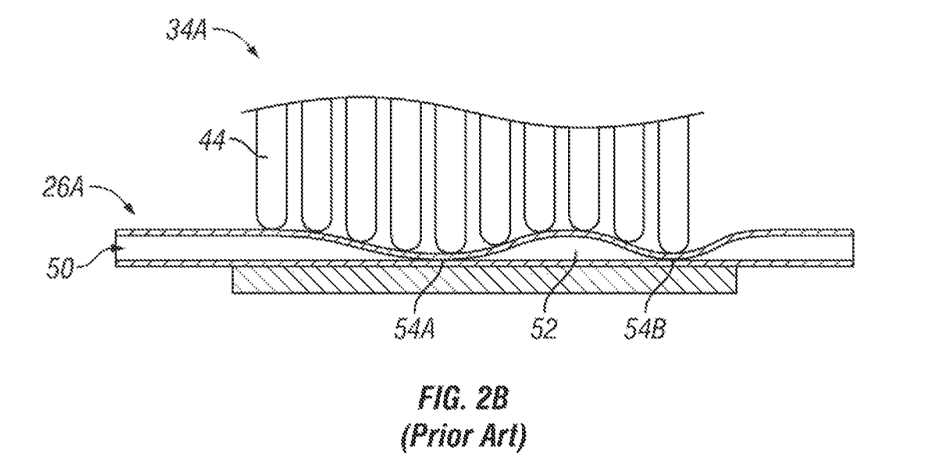

FIG. 1B depicts an exemplary IV set 20 according to certain aspects of the present disclosure. The IV set 20 includes a combined bag spike and drip chamber 22 configured to connect to a standard IV bag (not shown in FIG. 1B). In certain embodiments, a needleless connector replaces the bag spike 22 to connect to IV bags equipped with the appropriate mating needleless connector. The IV set 20 includes a check valve 23 and two needleless access ports 15, configured to allow fluidic connection of another fluid device or tube having an appropriate needleless connector to the IV set 20. In certain embodiments, the needleless connector 15 comprises a female Luer connector. The IV set 20 also includes a pumping segment 26 configured to mate with a peristaltic IV pump (not shown in FIG. 1B). The pumping segment 26 includes a resilient tube and locating fittings configured to place the resilient tube beneath the fingers of peristaltic pumping mechanism, such as shown in FIGS. 2A and 2B. The resilient tube is described in greater detail with respect to FIG. 3. The IV set also includes a needleless fitting 28 configured to connect to an infusion device (not shown), for example an IV cannula, adapted to introduce the medical fluid delivered through the IV set 20 into the body of the patient 10. All of the fittings and elements of IV set 20 are connected by tubing 24. In certain embodiments, the IV set 20 includes additional fittings, such as a manual flow control device. In certain embodiments, the IV set 20 does not include one or more of the elements shown in FIG. 1B. In certain embodiments, the IV set 20 comprises additional lines connected to one of the tubes 24 through a Y-fitting (not shown). In certain embodiments, one or more of the elements shown in FIG. 1B are replaced by other elements serving the same function.

FIGS. 2A and 2B are a perspective view and a cross-section view, respectively, of a peristaltic pumping mechanism 34A according to certain aspects of the present disclosure. In certain embodiments, the peristaltic pumping mechanism 34A is a part of the pump module 34 of FIG. 1A. The peristaltic pumping mechanism 34A comprises a series of cams 40 fixedly mounted on a shaft 42 that is rotated by a motor (not shown). In certain embodiments, the shaft 42 rotates at a constant speed. In certain embodiments, the shaft 42 rotates at a speed that varies over a single rotation. In certain embodiments, each of the cams 40 presses on followers or "fingers" 44 that are in contact with adjacent sections of the tube 26A of pumping segment 26. In certain embodiments, the portions of the fingers 44 that contact the tube 26A are curved in the direction perpendicular to the length of the tube. In certain embodiments, the same portions of the fingers that contact the tube 26A are flat in the direction perpendicular to the length of the tube. As each finger 44 descends, when displaced by rotation of the respective cam 40, the tube 26A is compressed between the finger 44 and a platen 46. The locating fittings of pumping segment 26 have been omitted in FIG. 2A so as not to obscure the disclosure, but serve to locate the tube 26A beneath the fingers 44.

FIG. 2B illustrates how the peristaltic motion of the fingers 44 forces fluid through the tube 26A so as to deliver the medical fluid to the patient 10. The fingers 44 move up and down, in the view of FIG. 2B, in a synchronized manner such that each adjacent finger 44 is a step ahead of the finger 44 on one side and a step behind the finger 44 on the other side. At the moment in time captured in FIG. 2B, the tube 26A has been pinched shut at two points 54A and 54B. A pocket of fluid 52 has been formed by the rebound of the tube 26A. As the fingers 44 directly over points 54A and 54B ascend and the fingers 44 to the immediate left of the ascending fingers 44 descend, the pocket 52 will move to the left. As this wave-like motion continues, the pocket 52 will be moved to the exit 50 of the pumping mechanism 34A and new pockets will have been formed and moved along in the same fashion. In this manner, a peristaltic pumping mechanism periodically delivers an amount of fluid equal to the volume of pocket 52. The time interval at which the pockets 52 of fluid are delivered is controlled by the rate of rotation of shaft 42.

The volume of pocket 52 is affected by the resilience of the tube 26A. If the tube 26A initially rebounds to a first shape having a first cross-sectional area and later, for example after a certain amount of use in an IV pump, the material of tubing 26A becomes fatigued and only rebounds to a second cross-sectional area that is less than the first area, then the volume of pocket 52 is lower than it was initially when the tube 26A was new. The amount of reduction in rebound may be influenced by the amount of overcompression of the tube 26A.

Figure 3:
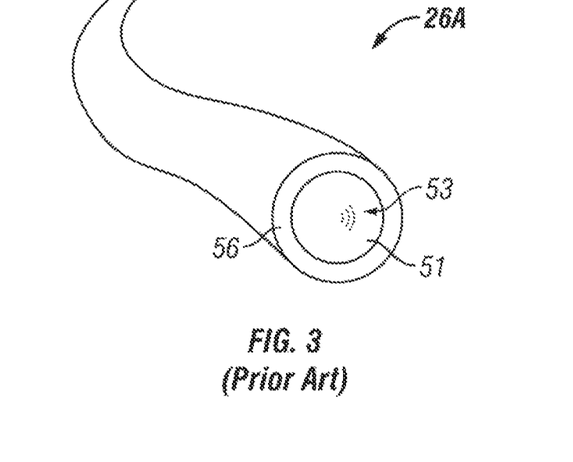
FIG. 3 is a perspective view of a standard round tube as used in existing IV sets.

FIG. 3 is a perspective view of a standard round tube 26A as used in existing IV sets 20. The tube 26A has an interior passage 53 with an interior surface 51 that is circular in profile. The tube wall 56 is of uniform thickness both around the cross-section and along the length of the tube 26A.

Figure 4A:
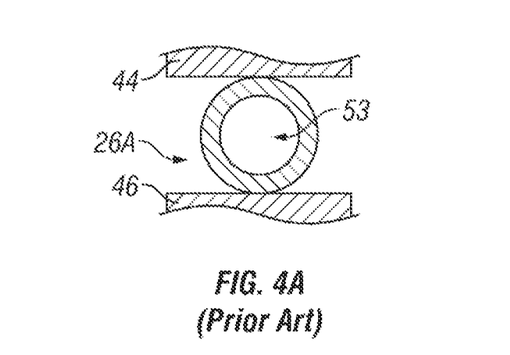
FIGS. 4A and 4B are cross-sectional views of the tube of FIG. 3 being manipulated by one of the peristaltic pumping fingers of FIGS. 2A and 2B.
Figure 4B:
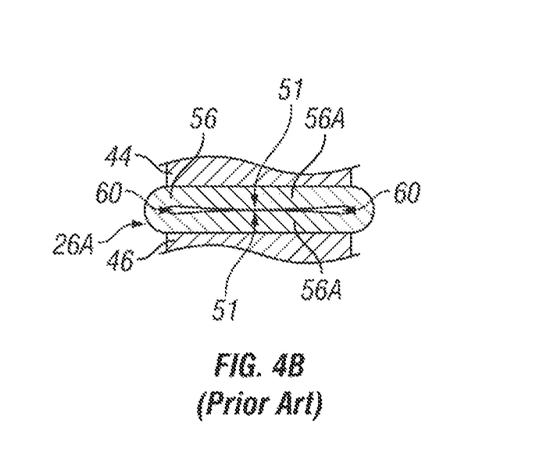

FIGS. 4A and 4B are cross-sectional view of the tube 26A of FIG. 3 being manipulated by one of the peristaltic pumping fingers of FIGS. 2A and 2B. FIG. 4A depicts the configuration of the tube 26A and the finger 44 and platen 46 when the finger 44 is in the fully "up" or "open" position. The tube 26A is in its fully expanded shape wherein the interior passage 53 has the largest cross-sectional area.

FIG. 4B depicts the configuration of the tube 26A when the finger 44 has descended and is compressing the tube 26A against the platen 46. The top portion of the interior surface 51 is touching the bottom portion of the same surface 51 in the middle of the tube 26A. Two gaps 60 remain at the edges of the interior passage 53 where the tube wall 56 has not been deformed sufficiently to form a sharp crease in the interior surface 51. The gaps 60 are sometimes referred to as "weeping" openings. Closing these gaps 60 requires sufficient force to distort the walls 56 and form a sharp crease in the interior surface 53 at the edges of the gaps 60.

Materials such as silicone have been used for the tube 26A in pumping segments 26 because silicone retains its resilience after repeated cycles of compression sufficient to distort the tube walls 46 and thereby form a liquid tight seal across the tube 26A. There is a desire to move away from silicones as materials in IV sets for reasons of cost reduction and the relatively high gas permeability of silicone with respect to other elastomers. Possible materials for use in pumping segments include thermoplastic elastomers such as polyurethane, ultra-high-weight polyvinyl chloride, and polyesters. Some of these materials, however, do not exhibit the resilient and rebound characteristics of silicone and therefore do not provide sufficient operational life under the levels of overcompression typically used with silicone tubes. Use of these materials is possible with a reduced level of compressive force that results in the reduction or elimination of overcompression of the material of the tube 26A.

Figure 5A:
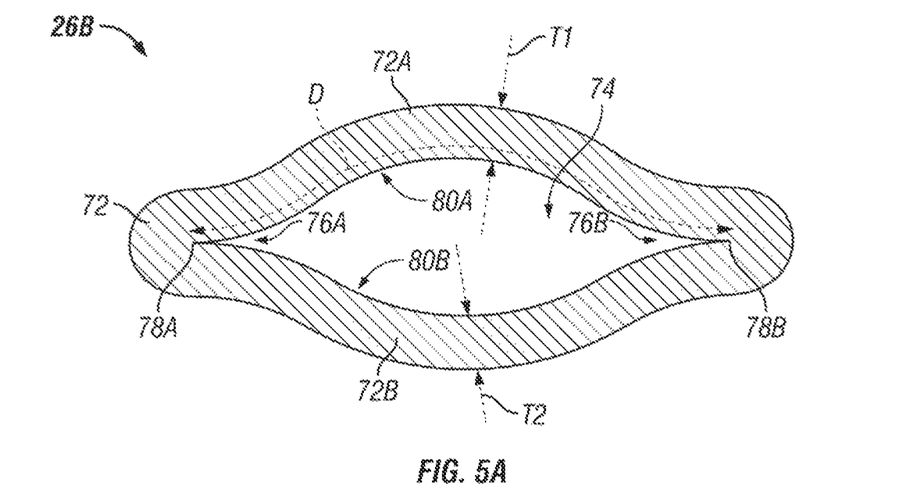
FIG. 5A is a cross-sectional view of a low-force pumping segment according to certain aspects of the present disclosure.

FIG. 5A is a cross-sectional view of a low-force pumping segment 26B according to certain aspects of the present disclosure. The interior passage 74 has a generally oval shape with, in this embodiment, two notches 76A, 76B on opposite sides of the interior surface 80. The notches 76A, 76B separate the interior surface 80 into a first surface 80A and a second. surface 80B. Each notch 76A, 76B has a respective tip 78A, 78B. The surfaces 80A and 80B approach each other asymptotically as the surfaces 80A, 80B near the tips 78A, 78B. The surfaces 80A, 80B meet and are sealed to each other at the tips 78A, 78B. The wall 72 of tube 26B has a first region 72A between the tips 78A, 78B on the side of interior surface 80A and a region 72B between the tips 78A, 78B on the side of interior surface 80B. Wall region 72A has a constant or substantially constant thickness T1 and wall region 72B has a constant or substantially constant wall thickness T2. In certain embodiments, the thicknesses T1 and T2 are equal. in certain embodiments, the interior surfaces 80A and 80B are of equal cross-section length D along the surfaces as indicated by the dashed-line arrow for surface 80A.

In certain embodiments, tube 26B is extruded with a shaped profile to form the notches 76 and tips 78. In certain embodiments, two separate sheets (not shown) form the first and second wall regions 72A and 72B and are bonded on both sides such that the edge of the bonded areas forms the tips 78.

Figure 5B:
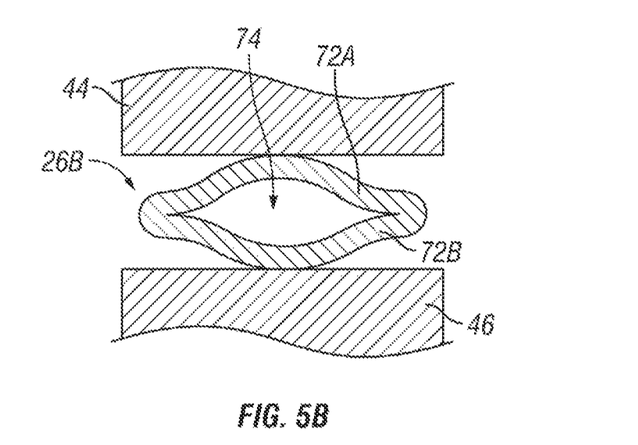
FIGS. 5B and 5C are cross-sectional views of the pumping segment of FIG. 5A being manipulated by one of the peristaltic pumping fingers of FIGS. 2A and 2B according to certain aspects of the present disclosure.
Figure 5C:
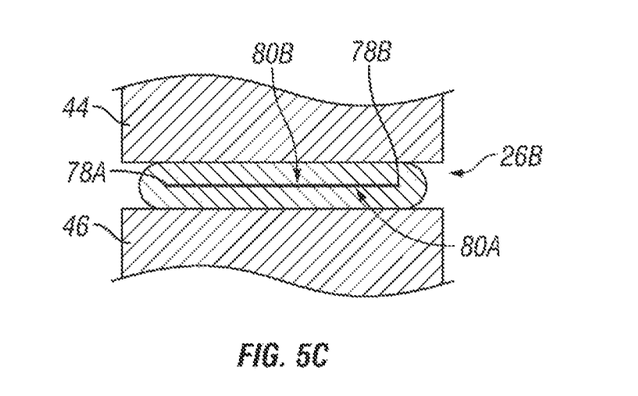

FIGS. 5B and 5C are cross-sectional views of the pumping segment 26B of FIG. 5A being manipulated by one of the peristaltic pumping fingers 44 of FIGS. 2A and 2B according to certain aspects of the present disclosure. FIG. 5B depicts the pumping segment 26B in the fully open position with the interior passage 74 having its maximum cross-sectional area. In certain embodiments, the first and second wall regions 72A, 72B are in contact only at the tips 78A, 78B when in the fully open position. In certain embodiments, the walls 72A, 72B are in continuous gapless contact from the tips 78A, 78B at least a portion of a distance towards a center of the tube 26B when in the fully open position.

As the finger 44 descends towards platen 46, the tube 26B is compressed between the finger 44 and platen 46. As the first wall region 72A is displaced towards the second wall region 76B, the length of the continuous gapless contact between the interior surfaces 80A and 80B extending from the tips 78A, 78B is increased in proportion to the displacement. FIG. 5C depicts the configuration of the tube 26B when the finger 44 has displaced the first wall region 72A sufficiently such that the interior surfaces 80A and 80B are in continuous gapless contact from tip 78A to tip 78B.

Where the prior art circular tube 26A formed gaps 60 at the ends of the contact between surfaces 51 in FIG. 4B, the tips 78A, 78B of tube 26B provide the sharp creases required to seal the contacting surfaces 80A, 80B without the need for the level of compressive force required to close the gaps 60 of a round tube 26A. In certain embodiments, the finger 44 of FIG. 5C descends sufficiently so as to form a gap between the finger 44 and platen 46 that is approximately equal to the sum of the respective thicknesses T1, T2 of the first and second wall portions 72A and 72B. In certain embodiments, it may be necessary to overcompress the tube 26B by a small amount, for example 2% of the sum of the respective thicknesses of the first and second portions 72A and 72B, in order to compensate for variation in wall thickness or surface smoothness of the inner surfaces 80A, 80B. In certain embodiments, the finger 44 of FIG. 5C descends sufficient to form a gap between the finger 44 and platen 46 that is approximately equal to 5% less than the sum of the thicknesses T1 and T2. In certain embodiments, the amount of force applied by the finger 44 to tube 26B is limited to the force sufficient to bring the interior surfaces 80A, 80B into continuous gapless contact across the entire distance between tips 78A and 78B. In certain embodiments, the amount of force applied by the finger 44 to tube 26B is limited to a force 10% greater than the force determined to be sufficient to bring the interior surfaces 80A, 80B into continuous gapless contact across the entire distance between tips 78A and 78B. In certain embodiments, the amount of force applied by the finger 44 to tube 26B is limited to the force 25% greater than the force determined to be sufficient to bring the interior surfaces 80A, 80B into continuous gapless contact across the entire distance between tips 78A and 78B.

Figure 6:
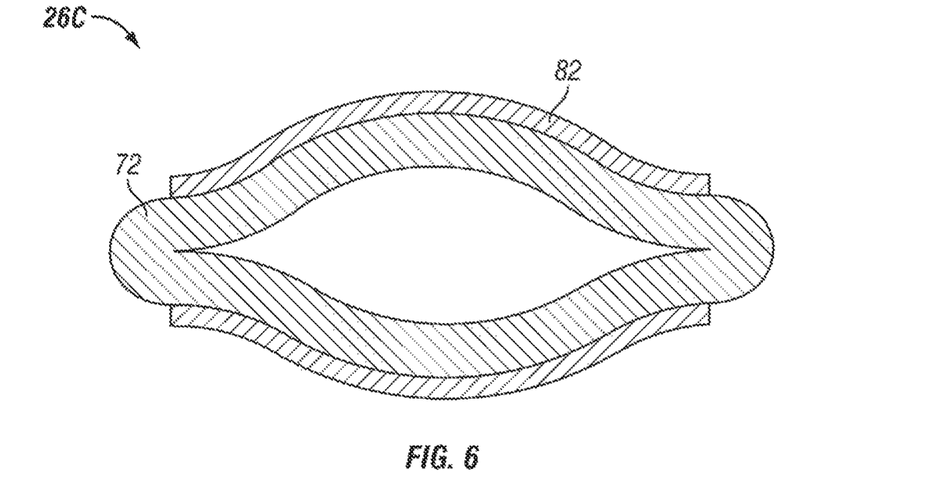
FIG. 6 is another embodiment of a low-force pumping segment according to certain aspects of the present disclosure.

FIG. 6 is another embodiment of a low-force pumping segment 26C according to certain aspects of the present disclosure. In certain embodiments, tube 26C has the same shape and features as tube 26B of FIG. 5A. Additionally, in certain embodiments, one or more spring elements 82 are coupled to the exterior of the tube wall 72 to provide at least a portion of the rebound characteristics required for the tube 26C to fully open when the compressive force is removed. In certain embodiments, two spring elements 82 are respectively coupled to the first and second wall regions 72A, 72B. In certain embodiments, the material of tube walls 72 are not resilient and form only a sealed passage 74 to contain the fluid. The tube wall 72 of FIG. 6 has the same profile as FIG. 5A with notches 76 and tips 78.

Figure 7:
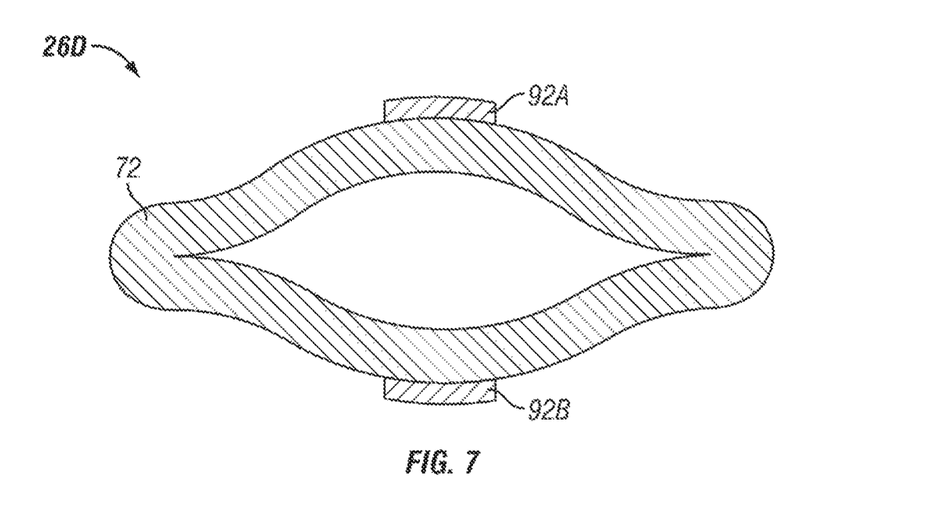
FIG. 7 is another embodiment of a low-force pumping segment according to certain aspects of the present disclosure.

FIG. 7 is another embodiment of a low-force pumping segment 26D according to certain aspects of the present disclosure. In certain embodiments, at least one coupling element 92 is coupled to the exterior of tube wall 72. In certain embodiments, two coupling elements 92A and 92B are coupled to the first and second wall regions 72A and 72B. The coupling elements are configured to couple to a pumping mechanism and be drawn apart by the pumping mechanism thereby separating the first and second wall regions 72A and 72B of the tube 26D. In certain embodiments, the coupling element 92 is magnetic and a magnetic driver (not shown) of the pumping mechanism attracts the magnetic coupling elements 92A, 92B and draws them apart as the finger 44 retracts. In certain embodiments, the coupling elements 92A, 92B have mechanical attachment features, such as Velcro®, that provide sufficient coupling strength to cause the walls regions 72A, 72B to separate during use while still being removable from the pumping mechanism 34A.

The disclosed low-force pumping segment provides an improved ability to shut off flow through the pumping segment by compression of the tube of the pumping segment using a reduced amount of force, compared to the force required to shut off flow through a circular tube. In certain embodiments, the tube of the low-force pumping segment has a pair of notches on opposite sides of the interior surface. The notches are shaped such that the surfaces on each side of the notch approach each other approximately asymptotically and come to a tip where the surfaces are sealingly joined. The shape of the gap between the two surfaces near the tip are configured such that the surfaces are in continuous and sealing contact with each other from each tip to points of first contact towards the center of the tube, wherein the points of contact on each side advance towards the center as the tube is compressed.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. A pumping segment with a low shut-off force, the pumping segment comprising:
   a medical-grade tube for delivering medical fluid, the tube comprising an interior surface comprising a first notch and a second notch on opposite sides of the interior surface such that the first and second notches divide a wall of the tube into a first wall region and a second wall region and divide the interior surface into a first interior surface and a second interior surface respectively forming interior surfaces of the first wall region and the second wall region;
   a magnetic coupling element coupled to a first exterior surface of the first wall region of the tube between the first and second notches, the first exterior surface separated from the first interior surface by a thicknesses of the first wall region, and the magnetic coupling element configured to magnetically couple to a pumping mechanism and be pulled by the pumping mechanism for separating the first and second wall regions of the tube; and
   an additional magnetic coupling element coupled to a second exterior surface of the second wall region of the tube between the first and second notches, the additional magnetic coupling element configured to magnetically couple to the pumping mechanism and be drawn apart from the magnetic coupling element by the pumping mechanism for separating the first and second wall regions of the tube.

2. The pumping segment of claim 1, wherein the second exterior surface is separated from the second interior surface by a thicknesses of the second wall region.

3. The pumping segment of claim 1, wherein:
   each notch of the first and second notches comprises a respective tip; and
   the first interior surface and the second interior surface asymptotically approach each other at each notch and sealingly meet at the tip of each notch.

4. The pumping segment of claim 3, wherein the first and second interior surfaces have equal widths.

5. The pumping segment of claim 3, wherein the notches are configured such that the first and second interior surfaces are in continuous gapless contact from the tips at least a portion of a distance towards a center of the tube when the first wall region of the tube is displaced toward the second wall region.

6. The pumping segment of claim 5, wherein:
   the first and second wall regions of the tube have constant respective wall thicknesses between the tips of the notches; and
   the first and second interior surfaces are in continuous gapless contact between the tips when the tube is compressed to a total thickness approximately equal to a sum of the respective thicknesses of the first and second wall regions.

7. The pumping segment of claim 1, wherein the tube is configured to elastically deform as the first wall region of the tube is displaced toward the second wall region and to separate the first wall region of the tube from the second wall region of the tube as the tube returns to an undeformed shape.

8. The pumping segment of claim 1, wherein the tube comprises a thermoplastic elastomer, a polyurethane, an ultra-high-weight polyvinyl chloride, a polyester, or a silicone.

9. An intravenous (IV) set with a low shut-off force, the IV set comprising:
   a medical-grade tube for delivering medical fluid, the tube having a tube wall comprising an interior surface comprising a first notch and a second notch on opposite sides of the interior surface, each notch comprising a tip, the first and second notches dividing the tube wall into first and second portions;
   a magnetic coupling element coupled directly to a first exterior surface of the first portion of the tube wall between the notches, the first exterior surface separated from a first interior surface of the first portion by a thickness of the first portion, and the magnetic coupling element configured to magnetically couple to a pumping mechanism and be pulled by the pumping mechanism for separating the first and second portions of the tube wall; and
   an additional magnetic coupling element coupled directly to a second exterior surface of the second portion of the tube wall between the notches, the additional magnetic coupling element configured to magnetically couple to a pumping mechanism and be and be drawn apart from the magnetic coupling element by the pumping mechanism for separating the first and second portions of the tube wall.

10. The IV set of claim 9, wherein the second exterior surface is separated from a second interior surface of the second portion by a thickness of the second portion.

11. The IV set of claim 9, wherein:
    each notch of the first and second notches comprises a respective tip; and
    the first interior surface and the second interior surface asymptotically approach each other at each notch and sealingly meet at the tip of each notch.

12. The IV set of claim 11, wherein the first and second interior surfaces have equal widths.

13. The IV set of claim 11, wherein the notches are configured such that the first and second interior surfaces are in continuous gapless contact from the tips at least a portion of a distance towards a center of the tube when the first portion of the tube is displaced toward the second portion.

14. The IV set of claim 13, wherein:
    the first and second portions of the tube wall have constant respective wall thicknesses between the tips of the notches; and
    the first and second interior surfaces are in continuous gapless contact between the tips when the tube is compressed to a total thickness approximately equal to a sum of the respective thicknesses of the first and second portions.

15. The IV set of claim 9, wherein the tube is configured to elastically deform as the first portion of the tube wall is displaced toward the second portion of the tube wall and to separate the first portion of the tube wall from the second portion of the tube wall as the tube returns to an undeformed shape.

* * * * *